United States Patent [19]

Meer

[11] Patent Number: 4,830,008

[45] Date of Patent: May 16, 1989

[54] METHOD AND SYSTEM FOR TREATMENT OF SLEEP APNEA

[76] Inventor: Jeffrey A. Meer, 7380 St. Auburn Dr., Birmingham, Mich. 48010

[21] Appl. No.: 156,186

[22] Filed: Feb. 16, 1988

Related U.S. Application Data

[63] Continuation-in-part of Ser. No. 41,973, Apr. 24, 1987.

[51] Int. Cl.$^4$ .................. A61N 1/00; H05G 00/00
[52] U.S. Cl. .................... 128/421; 128/721
[58] Field of Search ............. 128/419.6, 421, 716, 128/720, 721, 204.23, 905

[56] References Cited

U.S. PATENT DOCUMENTS

| | | | |
|---|---|---|---|
| 4,050,458 | 9/1977 | Friend | 128/204.23 |
| 4,365,636 | 12/1982 | Bakev | 128/716 |
| 4,433,693 | 2/1984 | Hochstein | 128/721 |
| 4,580,575 | 4/1986 | Birnbaum et al. | 128/716 |
| 4,619,270 | 10/1986 | Margolis et al. | 128/721 |
| 4,665,926 | 5/1987 | Leuner et al. | 128/716 |
| 4,694,839 | 9/1987 | Timme | 128/721 |

FOREIGN PATENT DOCUMENTS 8023619  11/1980  France ................ 128/419.6

Primary Examiner—Francis Jaworski
Assistant Examiner—George Manuel
Attorney, Agent, or Firm—Brooks & Kushman

[57] ABSTRACT

A method for treatment of sleep-apnea syndrome in a patient is disclosed as including mointoring inspiratory effort and generating electrical signals in response to the step of monitoring in order to stimulate those nerves which activate the patient's upper airway muscles to contract in order to maintain upper airway patency. A system (10) for such treatment is disclosed as including a monitor (14) capable of monitoring inspiratory effort, and an elecrtrical signal generating mechanism (16) coupled to the monitor (14) for generating electrical signals, to affect the patient's upper airway muscles in order to thereby maintain upper airway patency.

23 Claims, 3 Drawing Sheets

METHOD AND SYSTEM FOR TREATMENT OF SLEEP APNEA

CROSS REFERENCE TO RELATED APPLICATION

This invention is a continuation-in-part of prior application Ser. No. 041,973 which was filed Apr. 24, 1987 in the name of Jeffrey A. Meer.

TECHNICAL FIELD

This invention relates to a method and system for maintaining upper airway patency in human patients by stimulating those nerves which activate the patient's upper airway muscles.

BACKGROUND ART

Sleep-apnea syndrome is a medical condition characterized by daytime hypersomnolence, morning headaches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed "obstructive sleep apnea syndrome", is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. In addition, the medications frequently have distressing and sometimes dangerous side effects.

Surgical means have included uvulopalatopharyngoplasty, tonsillectomy, surgery to correct severe retrognathia and tracheostomy. These procedures may be effective but the risk of surgery in these patients can be prohibitive and the procedures are often unacceptable to these patients.

Physical measures have included weight loss, nasopharyngeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in *Direct Diaphragm Stimulation* by J. Mugica et al. PACE Vol. 10 Jan-Feb. 1987, Part II, *Preliminary Test of a Muscular Diaphragm Pacing System on Human Patients* by J. Mugica et al. from Neurostimulation: An Overview 1985 pp. 263-279 and *Electrical Activation of Respiration* by Nochomovitez IEE Eng. in Medicine and Biology, June, 1983.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue anteriorly down the throat choking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985 senses volume displaced by the lungs and stimulates the appropriate nerve to open the patient's glottis to treat dyspnea. This apparatus would not be effective for treatment of sleep apnea. The apparatus produces a signal proportional to the displaced air volume of the lungs and thereby the signal produced is too late to be used as an indicator for the treatment of sleep apnea. There is often no displaced air volume in sleep apnea due to obstruction.

The only measure which is completely effective in obstructive sleep apnea is tracheostomy, however, this operation carries considerable morbidity and is aesthetically unacceptable to many patients.

DISCLOSURE OF INVENTION

An object of the present invention is to provide a method and system for effective treatment of sleep apnea syndrome which is acceptable to patients in terms of aesthetics and comfort and avoids use of pharmacological measures or tracheostomy.

In carrying out the above objects, the method for treatment of sleep-apnea syndrome comprises monitoring inspiratory effort and generating electrical signals in response to the step of monitoring in order to stimulate those nerves which activate the patient's upper airway muscles to contract in order to maintain upper airway patency. The upper airway muscles include one or more in the group comprising geniohyoid, genioglossus, digastric, stylopharyngei or mylohyoid.

In one embodiment of the invention, monitoring inspiratory effort includes monitoring contraction of the patient's inspiratory muscles. The inspiratory effort monitored is analyzed by comparing the contraction of the patient's inspiratory muscles to a predetermined threshold contraction. Then an electrical signal is generated as necessary at the appropriate instant during the respiratory cycle to activate those muscles that move the patient's tongue anteriorly and maintain upper airway patency. At the same time, inspiration can be stimulated if necessary or inspiration alone can be stimulated by causing the diaphragm and other accessory muscles such as the sternomastoid muscles to contract when no inspiratory effort is sensed by the monitor.

In another embodiment of the invention, monitoring inspiratory effort includes monitoring intrathoracic pressure. The measured intrathoracic pressure measured is compared to a predetermined threshold of intrathoracic pressure and as necessary electrical signals are generated at the appropriate instant during the respiratory cycle to activate those muscles that move the patient's tongue anteriorly to maintain upper airway patency. At the same time, inspiration can be stimulated if necessary or inspiration alone can be stimulated by causing the diaphragm and other accessory muscles such as the sternomastoid muscles to contract when no inspiratory effort is sensed by the monitor.

A system for treatment of sleep-apnea syndrome in a patient comprises a monitor capable of monitoring inspiratory effort, and an electrical signal generating mechanism coupled to the monitor for generating electrical signals to effect those nerves which activate the patient's upper airway muscles to contract as necessary to thereby maintain upper airway patency.

In a preferred embodiment of the invention, upper airway muscle activity is sensed and if normal activity is sensed, the release of electrical signals is inhibited.

The system further includes a sensor lead having first and second ends. The first end is connected to the monitor and the second end includes a sensor electrode for gathering information from the inspiratory muscles and for transmitting the information gathered along the lead to the monitor. An effector lead having first and second ends is connected to the signal generating mechanism by the first end. The second end includes an effector electrode which transmits electrical signals generated by the electrical signal generating mechanism to those nerves which effect the upper airway muscles. The effector lead can also be connected to the monitor to sense action potentials in those nerves which innervate those muscles which maintain upper airway patency.

In one embodiment of the invention, the monitor monitors contraction of the patient's inspiratory muscles. In a second embodiment of the invention, the monitor monitors intrathoracic pressure.

In the preferred embodiment of the invention, the electrical signal generating mechanism is programmable with respect to voltage, current, pulse width and frequency of pulse emission.

The objects, features, and advantages of the present invention are readily apparent from the following detailed description of the best mode for carrying out the invention when taken with the accompanying drawings.

BEST MODE FOR CARRYING OUT THE INVENTION

Figure 1:
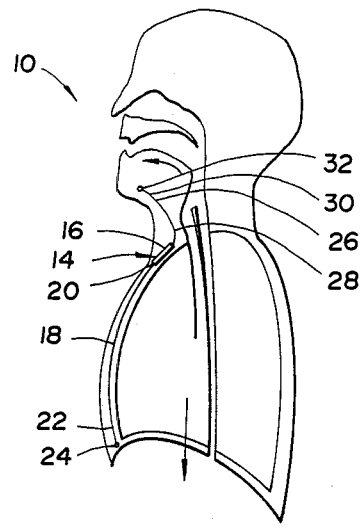
FIG. 1 is a cutaway view of a patient shown having a system for treatment of sleep apnea constructed in accordance with the present invention implanted subcutaneously and illustrating an electrical pulse generating device implanted in the pectoral region, a sensor electrode for sensing diaphragm action potential and an effector electrode for stimulating contraction of upper airway muscles.

Referring to FIGS. 1-5 of the drawings, a system for treatment of sleep apnea assembled in accordance with the present invention is generally indicated by reference numeral 10 as is used to monitor respiratory effort and generate electrical signals in response to the monitoring as necessary to stimulate nerves which activate a patient's upper airway muscles to contract in order to maintain upper airway patency.

As illustrated in FIG. 1, the system 10 comprises a monitor 14 capable of monitoring inspiratory effort. Monitor 14 is shown connected by lead 18 having first and second ends 20, 22 to a sensor electrode 24 located in the diaphragm region. Sensor electrode 24 detects action potential in the diaphragm and transmits that information to the monitor 14. An electrical signal generating mechanism 16 implanted subcutaneously, preferably in the right subclavian or pectoral area is coupled to the monitor 14 and generates electrical signals after interpreting input from the sensor electrode 24.

An effector lead 26 having first and second ends 28, 30 includes an effector electrode 32 at its second end. The effector electrode 32 is implanted into or around one or several motor nerves which are responsible for stimulating the respective upper airway muscles, or alternatively in or around the upper airway muscles. These muscles which include the geniohyoid, genioglossus, digastric, stylopharyngei or mylohyoid when stimulated contract and in contracting maintain patency of the oro-pharyngeal and/or naso-pharyngeal airway.

The effector electrode 32 is coupled via effector lead 26 to the generating mechanism 16 to receive the electrical signal to effect these upper airway muscles at the appropriate time during inspiration and under similarly appropriate circumstances to thereby maintain upper airway patency.

In a preferred embodiment of the invention, the system 10 and the sensor electrode 24 is actuable to act as an effector electrode to stimulate the inspiratory muscles if no inspiration is sensed by the monitor.

In the preferred embodiment of the invention shown in FIG. 1, the effector electrode 24 is connected to the genioglossus muscle or its respective motor nerve to move the tongue anteriorly and thereby prevent upper airway obstruction.

Figure 2:
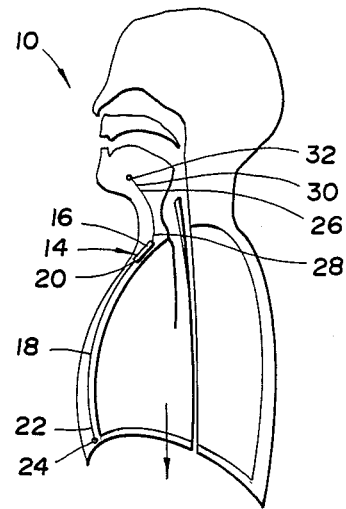
FIGS. 2 is a cutaway view of the patient shown in FIG. 1 illustrating a combined sensor/effector electrode for sensing and stimulating contraction of upper airway muscles.

With reference to FIG. 2 of the drawings, the effector electrode 32 also serves as a second sensor electrode to thereby sense activity in the upper airway muscles while the patient is awake to send signals to inhibit the electrical signal generating mechanism 16 from stimulating the upper airway muscles at inappropriate times. In this way the electrical signal generating mechanism 16 stimulates the effector electrode 32 if the upper airway muscles 12 are detected to be passive at the same time the inspiratory muscles are detected to be active thus detection of a predetermined level of action potential by the effector/sensor electrode would have an inhibitory effect on the electrical signal generating mechanism.

Figure 3:
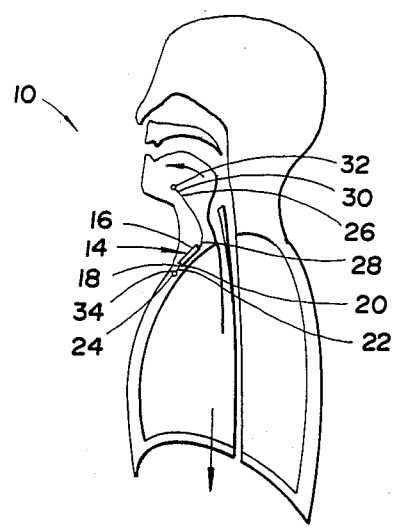
FIG. 3 is a cutaway view similar to FIG. 1 illustrating the sensor electrode connected to a pressure transducer located in the pleural space.

FIG. 3 illustrates sensor electrode 24 including a pressure sensitive receptor 34 at its distal end implanted into the thoracic cavity for monitoring intrathoracic pressure. Comparison to a certain predetermined threshold of negative pressure within the thorax due to airway obstructions during active inspiration triggers the electrical signal generating mechanism 16 to stimulate the upper airway muscles to create a patent airway.

Figure 4:
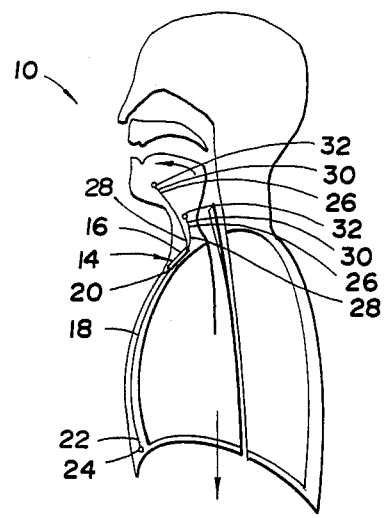
FIG. 4 is a cutaway view similar to FIG. 1 illustrating sensor/effector electrodes implanted in both hemi-diaphragms and an additional effector electrode located in the upper airway.

As shown in FIG. 4, two effector electrodes 32 have been implanted into the patient. The multiple effector electrodes 32 stimulate various muscles in the upper airway to maintain a patent upper airway simultaneously with stimulation of the diaphragm and other accessory muscles for inspiration such as the sternomastoid muscles to cause inspiration at a predetermined rate when no inspiratory effort is sensed by the monitor 14.

Figure 5:
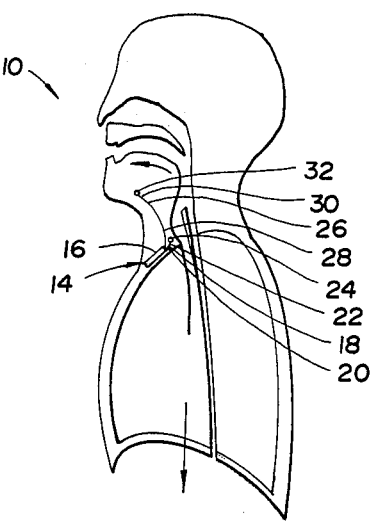
FIG. 5 is a cutaway view similar to FIG. 1 illustrating sensor and effector electrodes attached about the cervical portion of the phrenic nerve.

As shown in FIG. 5, the sensor electrode 24 is placed around the cervical portion of the phrenic nerve to detect action potentials in the phrenic nerve, i.e. incipient inspiration. The electrical signal generating mechanism 16 generates electrical signals based on information obtained from the phrenic nerve to maintain a patent airway in patients with obstructive sleep-apnea syndrome. In this arrangement, the electrical signal generating mechanism 16 may also act as a phrenic nerve stimulator in patients with central sleep-apnea syndrome.

Figure 6:
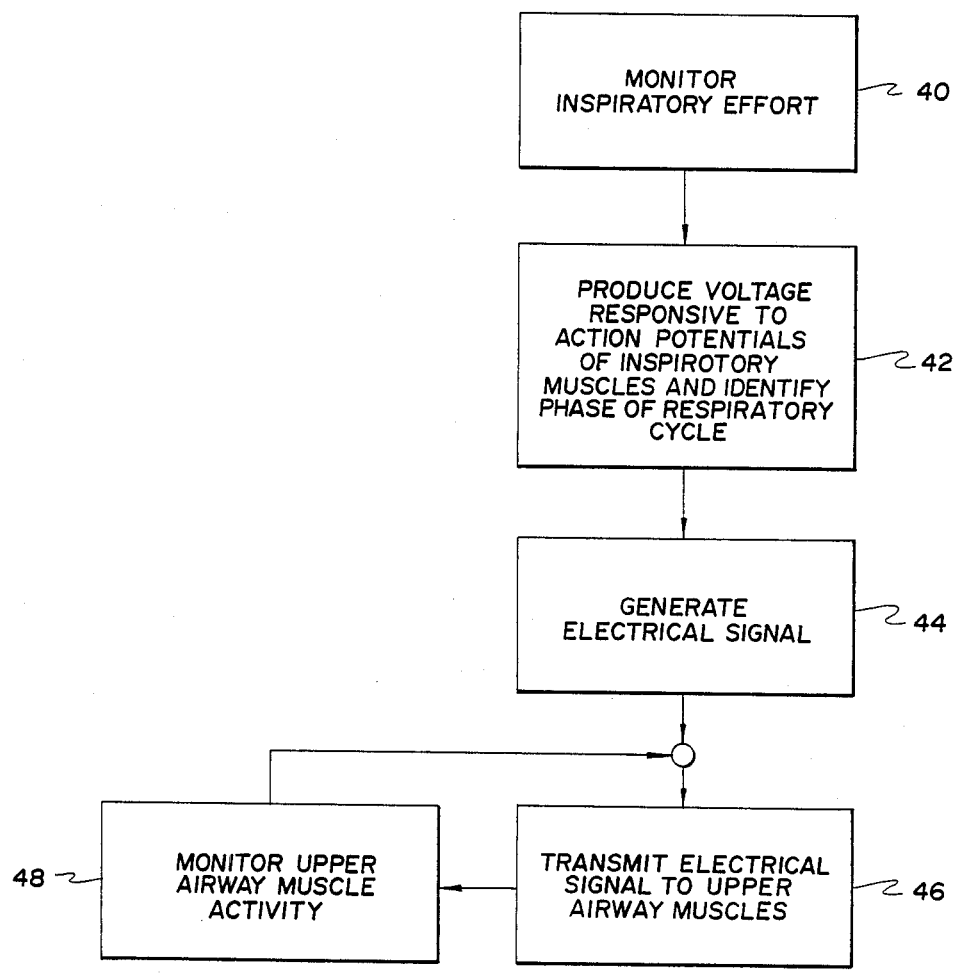
FIG. 6 is a flow diagram illustrating steps defining the method of the current invention.

As illustrated in FIG. 6 and shown sequentially in boxes numbered 40, 42, 44, 46, and 48, the method for treatment of sleep-apnea syndrome in a patient comprises the step of monitoring inspiratory effort. Inspiratory effort can be monitored by monitoring contraction of the diaphragm by electromyogram, sensing nerve conduction of the phrenic nerve, i.e. monitoring action potentials, monitoring intrathoracic pressure change via a pressure transducer, or by the use of an impedance pneumogram.

As shown in block 42, a voltage is produced responsive to the inspiratory efforts monitored and the phase of the respiratory cycle is identified. An electrical signal is generated, box 44, in response to the step of monitoring. As seen in box 46, those electrical signals are transmitted to stimulate those nerves which activate the patient's upper airway muscles to contract in order to maintain upper airway patency. Box 48 highlights a feature of the preferred embodiment wherein upper airway muscle activity is sensed and the release of electrical signals is inhibited if normal upper airway activity is detected.

OPERATION OF THE SYSTEM

The system 10 for treatment of sleep-apnea syndrome monitors inspiratory effort and generates electrical signals in response to the monitoring in order to stimulate nerves which activate the patient's upper airway muscles to contract in order to maintain upper airway patency. This is accomplished through the various embodiments of the aforementioned system 10.

The monitor 14 detects inspiratory effort by sensing action potentials in either the diaphragm or phrenic nerve or by sensing negative pressure in the thorax. The sensor electrode 24 which gathers this information passes it along lead 18 to the electrical signal generating mechanism 16 where that information is analyzed against a predetermined threshold. If the predetermined threshold is not met then an electrical signal is released by the electrical signal generating mechanism 16 and transmitted through lead 26 and effector electrode 32 to stimulate those nerves that effect those upper airway muscles which maintain upper airway patency. Effector electrodes 32 are located in the various upper airway muscles or around one or several of the nerves which stimulate those muscles and the effector electrode causes the muscles to contract when an electrical signal is received.

Preferably, the electrical signal generating mechanism 16 includes its own power supply such as a battery, not shown, typically of the lithium iodine type, batteries currently used in cardiac pacemakers. The electrical signal generating mechanism 16 and battery are enclosed in a hermetically sealed case with one or more sockets for insertion of sensor and effector leads 18, 26. Electrical signal generating mechanisms of MEDTRONIC, models 3014 and 3128, are suitable for use with the invention herein.

The sensor lead 18 conducts electrical signal impulses between the electrical signal generating mechanism 16 and various nerves or muscles. The sensor lead 26 may be tunneled subcutaneously and the distal end of the sensor electrode 18 implanted into one of the various inspiratory muscles, including but not limited to the diaphragm, intercostal muscles, sternomastoid muscles, or around the nerves responsible for stimulation of those respiratory muscles. The sensor electrode 18 serves as a sensor to detect when inspiratory effort commences and may also serve as an effector electrode for stimulating respiratory muscles in patients with central sleep apnea.

The sensor and effector leads 18, 26 may be wires made of metal alloy to allow good conductivity. The leads 18, 26 should be fatigue resistant, may be coiled to increase flexibility, and may be multifiller to provide redundancy within the lead. The wire must be insulated with materials such as Silastic or polyurethane and only the metal electrode at the distal end is actually exposed. Similar leads 18, 26 are currently used in cardiac pacemakers.

Most preferably, the effector electrode 32 effects the nerves which stimulate the genioglossus muscle to move the tongue anteriorly and thus prevent upper airway obstruction when an electrical signal is received. The effector lead 26 can also include a sensor to transmit a signal to the electrical signal generating mechanism 16 to inhibit electrical signal generation at any inappropriate times such as when the patient is awake when normal genioglossus muscle action potentials will be sensed by the device which will inhibit the electrical signal generating mechanism 16.

Preferably, the electrical signal generating mechanism 16 is a digital device which may be programmed. The digital technology is used to create timing circuits and programming circuits such that electrical impulses may be programmed to be transmitted at specific times. This allows the electrical signal generating mechanism 16 to discharge electrical signals at a predetermined rate, for instance, for use in patients with central sleep apnea, or in synchrony with inspiratory effort in patients with obstructive sleep apnea. A programmable electrical signal generating mechanism 16 may be programmed externally by the use of pulsed magnetic fields or radio frequency signals similar to those utilized in current cardiac pacemakers. Preferably, metallic oxide semiconductor circuitry is utilized such that the electrical signal generating mechanism will operate at low energy levels and enhance miniaturization.

While the best mode for carrying out the invention has been described in detail, those familiar with the art to which this invention relates will recognize various alternative designs and embodiments for practicing the invention as defined by the following claims.

What is claimed is:

1. A method for treatment of sleep-apnea syndrome in a patient, the method comprising the steps of:
   monitoring inspiratory effort;
   generating electrical signals in response to the step of monitoring; and
   applying said electrical signals to those nerves which activate the patient's upper airway muscles to contract in order to maintain upper airway patency.

2. A method as in claim 1 further including the step of sensing upper airway muscle activity and inhibiting the release of electrical signals if normal upper airway activity is detected.

3. A method as in claim 1 or 2 further including the step of activating those muscles included in the group consisting of the diaphragm or sternomastoid muscles as necessary to cause inspiration at a predetermined rate when no inspiratory effort is sensed by said monitor.

4. A method as in claim 1 wherein the upper airway muscles include one or more of the muscles in the group consisting of geniohyoid, genioglossus, digastric, stylopharyngei or mylohyoid.

5. A method as in claim 4 wherein effecting the upper airway muscles includes moving the patient's tongue anteriorly.

6. A method as in claim 1 wherein monitoring inspiratory effort includes monitoring contraction of the patient's inspiratory muscles.

7. A method as in claim 6 wherein monitoring the inspiratory effort includes comparing the contraction of the patient's inspiratory muscles to a predetermined threshold contraction.

8. A method as in claim 7 wherein the electrical signals are generated at the appropriate instant during the respiratory cycle.

9. A method as in claim 1 wherein monitoring inspiratory effort includes monitoring intrathoracic pressure.

10. A method as in claim 9 wherein monitoring the inspiratory effort sensed includes comparing the intrathoracic pressure to a predetermined threshold of intrathoracic pressure.

11. A method as in claim 9 wherein the electrical signals are generated at the appropriate instant during the respiratory cycle.

12. A system (10) for treatment of sleep-apnea syndrome in a patient comprising:
monitoring means (14) capable of monitoring inspiratory effort; and
electrical signal generating means (16) coupled to said monitor (14) for generating electrical signals to effect those nerves which activate the patient's upper airway muscles to contract as necessary to thereby maintain upper airway patency.

13. A system as in claim 12 wherein said monitor (14) senses action potentials in those nerves which innervate those muscles which maintain upper airway patency.

14. A system (10) as in claim 12 or 13 further including a sensor lead (18) having first and second ends (20, 22); said first end (20) being communicated to said monitor (14) and said second end (22) including a sensor electrode (24) attached to the inspiratory muscles for receiving inspiratory information from the inspiratory muscles and for conveying the information received by said sensor electrode (24) along lead (18) to said monitor (14).

15. A system (10) as in claim 14 further including an effector lead (26) having first and second ends (28, 30); said first end (28) being connected to said electrical signal generating means (16) and said second end (30) including an effector electrode (32) for transmitting electrical signals sent via effector lead (26) to those nerves which activate the upper airway muscles.

16. A system as in claim 15 wherein said effector lead (26) is also communicated to said monitor via said electrical signal generating means 16 (14) to sense action potentials at the effector electrode (32) in those nerves which innervate those inspiratory muscles which maintain upper airway patency.

17. A system (10) as in claim 16 wherein said effector electrode (32) initiates excitation in one or more of the muscles in the group consisting of geniohyoid, genioglossus, digastric, stylopharyngei or mylohyoid.

18. A system (10) as in claim 17 wherein said effector electrode (32) initiates excitation in the genioglossus muscle and thereby moves the patient's tongue anteriorly.

19. A system (10) as in claim 14 wherein said monitor (14) monitors contraction and expansion of the patient's inspiratory muscles.

20. A system (10) as in claim 14 wherein said monitor (14) monitors intrathoracic pressure.

21. A system (10) as in claim 14 wherein said electrical signal generating means (16) is programmable with respect to providing electrical stimuli output in response to predetermined input messages.

22. A system (10) as in claim 21 wherein said programmable electrical signal generating means (16) is programmable with respect to voltage, current, pulse width and frequency of electrical stimuli provided.

23. A method of the type used to treat sleep-apnea syndrome including monitoring inspiratory effort characterized by generating electrical signals in response to the monitoring to stimulate those nerves which activate the patient's upper airway muscles to contract thereby to maintain upper airway patency and sensing upper airway muscle activity and inhibiting the release of electrical signals if normal upper airway activity is detected.

* * * * *